(12) United States Patent
Gilding et al.

(10) Patent No.: US 6,258,995 B1
(45) Date of Patent: Jul. 10, 2001

(54) WOUND TREATMENT COMPOSITION

(75) Inventors: Denis K. Gilding; Yimin Qin, both of Cheshire (GB)

(73) Assignee: Advanced Medical Solutions Limited, Winsford (GB)

( * ) Notice: Subject to any disclaimer, the term of this patent is extended or adjusted under 35 U.S.C. 154(b) by 0 days.

(21) Appl. No.: 08/983,379

(22) PCT Filed: Jul. 19, 1996

(86) PCT No.: PCT/GB96/01719

§ 371 Date: Jan. 12, 2000

§ 102(e) Date: Jan. 12, 2000

(87) PCT Pub. No.: WO97/03710

PCT Pub. Date: Feb. 6, 1997

(30) Foreign Application Priority Data

Jul. 19, 1995 (GB) .................................... 9514838
Aug. 18, 1995 (GB) .................................... 9516925

(51) Int. Cl.$^7$ ........................................... A61F 13/00
(52) U.S. Cl. ................ 602/48; 602/41; 602/42; 602/43
(58) Field of Search ........................................ 602/41–48

*Primary Examiner*—Michael A. Brown
*Assistant Examiner*—Lalita M Hamilton
(74) *Attorney, Agent, or Firm*—Woodard, Emhardt, Naughton, Moriarty & McNett

(57) ABSTRACT

A wound treatment composition comprises an amorphous hydrogel incorporating fibers which have provided cations for cross-linking the hydrogel and a bacteria static agent. The composition has a viscosity of 20,000 to 1,000,000 cPs.

19 Claims, No Drawings

WOUND TREATMENT COMPOSITION

The present invention relates to compositions which are useful in the treatment of wounds. The invention relates more particularly to such compositions in the form of an amorphous hydrogel.

A hydrogel is a cross-linked macromolecular network swollen with water or biological fluids. An amorphous hydrogel is a partially cross-linked macromolecular network that has the three dimensional stability of a gel but still has the flow characteristics of a viscous fluid.

WO-A-96/13285 (Innovative Technologies) discloses dehydrated hydrogels produced by dispersing fibres into an aqueous solution of a hydrogel precursor incorporating a plasticiser. The fibres incorporate cations which are capable of cross-linking said precursor material to form a hydrogel. Water is then evaporated to produce a dehydrated hydrogel incorporating said fibres, the dehydrated hydrogel being cross-linked by said cations. The dehydrated hydrogel may be in the form of a film or a sheet. In the process described in the aforementioned application, the amount of hydrogel precursor used in the initial solution (comprising the precursor, plasticiser, fibres and water) is about 0.5%. This gives an amorphous hydrogel with a viscosity of usually less than 1,000 cPs prior to conversion of that amorphous hydrogel to the final dehydrated hydrogel. Such low viscosity amorphous hydrogels are not suitable as wound treatment compositions.

According to a first aspect of the present invention there is provided a wound treatment composition comprising an amorphous hydrogel incorporating fibres which have provided cations for cross-linking the hydrogel and a bacteriostatic agent, the composition having a viscosity of 20,000 to 1,000,000 cPs.

Viscosity may be measured in a Brookefield Viscometer using Spindle No. 4.

The viscosity of compositions of the invention is such that the compositions are are capable of being spread easily and evenly and may therefore be used as wound treatment compositions. Compositions in accordance with the invention are capable of absorbing exudate from a highly exuding wound and are capable of donating water to a relatively "dry" wound. The fibres stabilise the viscosity of the gel (without effecting its flow characteristics) and provide good coherent strength even when the amorphous hydrogel absorbs exudate. The cations provided by the fibres may be calcium cations so as to provide a controlled release of $Ca^{2+}$, into the matrix as the $Na^+$ concentration from the exudate rises.

When the amorphous hydrogel dries, the fibre reinforces the dry gel which may then be removed easily from a wound.

Compositions in accordance with the invention are particularly useful in the treatment of cavity wounds, e.g. decubitus ulcers. The compositions are introduced into the wound and pressed firmly into the base thereof. For preference the wound is then covered and sealed by a film having a high MVTR, typically 3,000 to 20,000 $gm^{-2}$ 24 $hr^{-1}$ (e.g. Hyderderm (ex Wilshire Medical) or IT425 or IT625 (ex Innovative Technologies)). The composition may also be used in the treatment of sinuses.

Amorphous hydrogels in accordance with the invention may be produced by admixing water, a hydrogel precursor material, a bacteriostatic agent, and fibres incorporating cations which are capable of cross-linking the precursor material to form an amorphous hydrogel having the fibres disposed throughout the hydrogel. The amounts of hydrogel precursor material in the admixture will be higher than those used in the preparation of the dehydrated hydrogel. Typically the hydrogel precursor will provide at least 1%, and more usually at least 2% of the admixture. The exact amount of the hydrogel precursor used will depend on the viscosity required for the amorphous hydrogel.

Preferred compositions in accordance with the invention have a viscosity in the range 500,000 to 1,000,000 cPs.

Examples of hydrogel precursor material which may be used include sodium alginate, sodium carboxymethyl cellulose, sodium pectinate, sodium O-carboxymethyl chitosan (OCC), sodium N,O-carboxymethyl chitosan (NOCC), sodium polyacrylate, and naturally occurring gums and synthetic polymers containing pendant carboxylic acid groups (hummectants).

The hydrogel precursor may consist wholly or partially of the Ace Mannas or other component of Alloe Vera) which is a natural polymer known to accelerate healing of wounds. The Ace Mannas may, for example, provide up to 80% of the matrix. The Ace Mannas may be clinical grade material obtainable from Carrington Laboratories, Dallas, Tex., USA. Ace Mannas is particularly suitable for use in admixture with sodium alginate and/or sodium pectinate as hydrogel precursor. Combinations of the above precursors may also be used.

If desired, the hydrogel precursor material may be admixed with another water soluble polymer such as hydroxypropyl cellulose or hydroxyethyl cellulose to provide the required viscosity properties for the final, amorphous hydrogel.

The fibres which are used contain a di- or higher valent cation which is effective for cross-linking the hydrogel. Examples of suitable cations include $Ca^{2+}$, $Zn^{2+}$, and cations which also act as enzyme cofactors. Particular preferred examples of fibres which may be used are calcium alginate fibres. The fibres will generally have a length of 1 to 80 mm and a thickness of 10 to 50 microns.

The fibres may be such that they absorb water from the aqueous solution of the hydrogel precursor material during manufacture of the amorphous hydrogel.

The bacteriostatic agent is preferably propylene glycol.

Typically amorphous hydrogels in accordance with the invention will comprise 0.5% to 5% of fibre, 1% to 5% of polymer forming the gel, 10% to 30% of the bacteriostatic agent, and a balance substantially of water, the percentages being by weight. A particularly preferred amorphous hydrogel comprises about 2% of fibre, about 2.5% of polymer forming gel, about 15% of the bacteriostatic agent, and a balance substantially of water, the percentages again being on a weight basis.

In a typical method of preparing an amorphous hydrogel in accordance with the invention, the fibres, polymer and bacteriostatic agent in their relative requisite amounts are admixed with water. Preferably the fibres and polymer together provide 4–6% (e.g. about 5%) by weight of the resultant mixture.

If desired the mixture may also incorporate an agent to enhance the swelling of the fibres and/or assist the dispersion thereof. A suitable agent is a citrate salt, particularly sodium citrate. Other examples include sodium chloride. The agent is preferably used in an amount up to 0.5%, preferably about 0.1% by weight.

After thorough mixing the dispersion may be filled into sachets or squeeze bottles of appropriate size for subsequent use as a wound treatment composition.

If desired, the amorphous hydrogel may incorporate an active agent (e.g. an antimicrobial agent, growth factor, connective tissue matrix degradation inhibitor or other cythokine).

The invention will be further described by the following non-limiting Examples.

EXAMPLE 1

1 kg of calcium alginate fibres having a length of about 10 mm, 1.2 kg of sodium alginate and 50 g of sodium citrate were dispersed in a mixture of 40 liters of water and 8.5 kg of propylene glycol. Thorough mixing produced an amorphous hydrogel having a viscosity of 800,000 cP.

The product was eminently suitable for use as a wound treatment composition.

EXAMPLE 2

6 grams of MF1-2B calcium alginate fibres (ex Innovative Technologies) were cut to a length of about 10 to 15 mm. The fibres were mixed together with 3 grams of sodium alginate powder (HF120 ex Pronova Biopolymers), 20 grams of hydroxypropyl cellulose (ex Hercules), 85 grams of propylene glycol, 0.5 grams of NaCl and 385.5 grams of distilled water.

The resultant gel was highly viscous (viscosity about 800,000 cps) and could be sterilised by autoclaving at 115° C.

The gel had significant water donating properties and had the general characteristics of a fibrous gel. The gel was eminently suitable as a wound treatment compositions.

What is claimed is:

1. An amorphous hydrogel incorporating fibres which have provided cations for cross-linking the hydrogel and a bacteriostatic agent the composition having a viscosity of 20,000 to 1,000,000 cPs.

2. A hydrogel as claimed in claim 1 comprising 0.5% to 5% by weight of fibres, 1% to 5% by weight of polymer forming the gel, 10% to 30% by weight of bacteriostatic agent, and a balance substantially of water.

3. A hydrogel as claimed in any claim 2 comprising about 2% of fibre, about 2.5% of polymer forming the gel, about 15% of the bacteriostatic agent, and a balance substantially of water.

4. A hydrogel as claimed in any one of claims 1 to 3 having a viscosity of 500,000 to 1,000,000 cPs.

5. A hydrogel as claimed in claim 1 wherein the bacteriostatic agent is propylene glycol.

6. A hydrogel as claimed in claim 1 wherein the fibres have a length of 1 to 80 mm.

7. A hydrogel as claimed in claim 1 wherein the fibres have a thickness of 10 to 50 microns.

8. A hydrogel as claimed in claim 1 for use as a wound treatment composition.

9. A method of producing an amorphous hydrogel comprising admixing an aqueous solution of a hydrogel precursor material, a bacteriostatic agent, and fibres incorporating cations which are capable of cross-linking said precursor material to form an amorphous hydrogel having fibres dispersed therein.

10. A method as claimed in claim 9 wherein the hydrogel precursor material is selected from sodium alginate, sodium carboxymethyl cellulose, sodium pectinate, sodium O-carboxymethyl chitosan (OCC), sodium N,O-carboxymethyl chitosan (NOCC), sodium polyacrylate, and naturally occurring gums and synthetic polymers containing pendant carboxylic acid groups (hummectants), Ace Mannas and mixtures thereof.

11. A method as claimed in claim 9 wherein the hydrogel precursor material is used in admixture with hydroxyethyl cellulose or hydroxypropyl cellulose.

12. A method as claimed in claim 9 wherein the admixture incorporates an agent to enhance the swelling of the fibres and/or assist the dispersion thereof.

13. A method as claimed in claim 12 wherein the agent is used in an amount up to 0.5% by weight.

14. A method as claimed in claim 12 wherein the agent is sodium citrate.

15. A method as claimed in claim 9 wherein the fibres contain $Ca^{2+}$, $Zn^{2+}$ and/or cations which also act as enzyme cofactors.

16. A method as claimed in claim 9 wherein the fibres are calcium alginate fibres.

17. A drug delivering system for delivering active agents to a wound site comprising an amorphous hydrogel as claimed in claim 1 and an active agent to be delivered to the wound.

18. A system as claimed in claim 17 wherein the active agent is an anticrobial agent, growth factor, connective tissue matrix degradation inhibitor or other cytokine.

19. An amorphous hydrogel incorporating fibres which have provided cations for cross-linking the hydrogel the composition having a viscosity of 20,000 to 1,000,000 cPs.

* * * * *